United States Patent [19]

Christen et al.

[11] Patent Number: 5,019,504

[45] Date of Patent: May 28, 1991

[54] PRODUCTION OF TAXOL OR TAXOL-LIKE COMPOUNDS IN CELL CULTURE

[75] Inventors: Alice A. Christen, Metairie; Donna M. Gibson, New Orleans; John Bland, Kenner, all of La.

[73] Assignee: The United States of America as represented by the Secretary of Agriculture, Washington, D.C.

[21] Appl. No.: 327,493

[22] Filed: Mar. 23, 1989

[51] Int. Cl.$^5$ .................... C12P 17/02; C12P 1/00; C12N 5/02; C12N 5/04

[52] U.S. Cl. ........................... 435/123; 435/41; 435/240.4; 435/240.46; 435/240.48; 549/510

[58] Field of Search ............... 435/41, 123, 240.4, 435/240.46, 240.48; 549/510

[56] References Cited

U.S. PATENT DOCUMENTS 4,152,214  5/1979  Delfel et al. ................... 195/104
4,910,138  3/1990  Miura et al. ................... 435/119

OTHER PUBLICATIONS

N. E. Delfel & J. A. Rothfus, "Antitumor Alkaloids in Callus Cultures of *Cephalotaxus Harringtonia*," Phytochemistry 16:1595–1598, (1977).

C. H. O. Huang et al., "New Taxanes from *Taxus Brevifolia*, 2", J. Nat. Prod. 49(4):665–669, (1986).

M. C. Wani et al., "Plant Antitumor Agents. VI. The Isolation and Structure of Taxol, a Novel Antileukemic and Antitumor Agent from *Taxus Brevifolia*," J. Am. Chem. Soc. 93(9):2325–2327, (1971).

Eilert et al., (1985), J. Plant Physiol. 119:65–76.

Gamborg et al., (1981), in T. A. Thrope, ed., Plant Tissue Culture, Academic Press, N.Y., p. 24.

Frank DiCosmo et al., "Plant Cell Cultures and Microbial Insult: Interactions with Biotechnological Potential," Trends in Biotechnology 3(5): 110–111, (1985).

Wolfgang, G. W. Kurz, "Semicontinuous Metabolite Production Through Repeated Elicitation of Plant Cell Cultures: A Novel Process," Plant Biotechnology ed. Tom J. Mabry, The University of Texas at Austin, pp. 93–103, 1–5, 202–203, (date unknown).

Margaret Collinge, "Ways and Means to Plant Secondary Metabolites," Trends in Biotechnology 4: 299–301, (Dec. 1986).

M. Tabata, "Recent Advances in the Production of Medicinal Substances by Plant Cell Cultures," In Plant Tissue Culture and its Bio-Technological Application, ed. W. Barz et al., Springer-Verlag, New York, pp. 3–16, (1977).

M. A. Zenkteler et al., "Cytological Studies on Regenerating Mature Female Gametophyte of *Taxus Baccata* and Mature Endosperm of *Tilia Platyphyllos* in in vitro Culture," Acta. Soc. Bot. Pol. 39(1); 161–173, (1970): Chem. Abst. 74:225, (1971).

*Primary Examiner*—Elizabeth C. Weimar
*Assistant Examiner*—Che S. Chereskin
*Attorney, Agent, or Firm*—M. Howard Silverstein; John D. Fado; Curtis P. Ribando

[57] ABSTRACT

Tissue of *Taxus brevifolia* has been successfully cultured to produce taxol, related alkaloids, and alkaloid precursors. These procedures will provide a supply of chemotherapeutic agents.

18 Claims, No Drawings

PRODUCTION OF TAXOL OR TAXOL-LIKE COMPOUNDS IN CELL CULTURE

BACKGROUND OF THE INVENTION

1. Field of the Invention

This invention relates to the production and recovery of alkaloid compounds by cell culture of the tissues of the conifer, *Taxus brevifolia* and other species of Taxus.

2. Description of Prior Art

Among the alkaloids which have been isolated from *T. brevifolia* plant material are taxol and a number of its derivatives [Horwitz et al., Ann. New York Acad. Sci. 466: 733–745 (1986); Suffness et al., In "The Alkaloids," Brossi, A. (ed.), Chemistry and Pharmacology 25: 6–18, 280–288 (1985)]. Taxol has been found to exhibit significant antitumor activity in a variety of cell lines, including B16 melanoma and Mx-1 mammary xenograft. Taxol completed Phase I clinical trials and in 1985 was approved for broader efficacy studies in Phase II trails. Phase II studies in ovarian cancer have shown taxol to be effective, with a response rate of 30% [Rowinsky et al., Proc. Am. Soc. Clin. Oncologists 7: 136, Abstr. 523 (1988)]. Some results were seen in patients with melanoma as well [Einsig et al., Proc. Am. Soc. Clin. Oncologists 7: 249, Abstr. 963 (1988)]. The mode of action of taxol is thought to be novel.

Continued testing of the drug and subsequent commercial applications of chemotherapy require quantities which cannot be obtained from the scarce natural source. Taxol is a complex compound, and attempts at chemical synthesis to date have been unsuccessful. Preparation of derivatives will depend on a supply of the parent compound from natural sources. The *T. brevifolia* tree is rare, has slow growth, and is not cultivated. Ten thousand pounds of bark are required to produce one pound of taxol. The extraction of the bark is complicated, and product variability occurs.

SUMMARY OF THE INVENTION

We have now surprisingly discovered that dedifferentiated or callus cells from *T. brevifolia* tissues can be successfully grown on artificial media and that the same chemotherapeutically active alkaloids are produced in culture as in the intact plant. Several new compounds are also produced. Previous studies indicate that, in many cases, plants do not produce the same compounds in culture that they do as intact plants [Benjamin et al., Planta Medica 23: 394–397 (1973)]. Our method of taxol production comprises the following steps:

a. providing living tissue of Taxus species;

b. providing a nutrient culture medium suitable for callus formation from said tissue and for suspension cell growth;

c. culturing said tissue on said medium to produce callus from said tissue and for suspension cell growth;

d. recovering taxol and related compounds from said callus and suspension cells and from said medium.

Optionally, an inducer may be added to step (c), thereby optimizing the production of taxol and related alkaloids.

Finding taxol in the cell cultures was unexpected insofar as it is normally found in the tree bark. Production of taxol by cell culture assures an adequate supply of the drug for chemotherapy. The taxol was found in the culture supernatant and was easily extracted with ether or methylene chloride. It was also recovered by adsorption to beads, prior to extraction. This simple recovery and extraction as compared to processing tree bark is an additional advantage in commercial production.

It is therefore an object of this invention to grow cells from *T. brevifolia* tissues in callus and suspension culture, and in further scale-up cultures.

It is also an object of the invention to produce chemotherapeutically active alkaloids, or their precursors or derivatives, in the culture medium as well as from the callus tissue or in cells.

Another object of the invention is to recover alkaloids from the culture medium as well as from the callus tissue or cells.

A further object of the invention is to produce new alkaloid compounds.

Other objects and advantages of the invention will become readily apparent from the ensuing description.

DETAILED DESCRIPTION OF THE INVENTION

The plant material of this invention which is especially useful for producing alkaloids is obtained from the Pacific yew, *Taxus brevifolia*. Any plant in this genus would produce the desired results. Tissue from any part of the plant, including the bark, cambium, needles, stems, seeds, cones, and roots, may be selected for inducing callus. However, for optimum yield of taxol, bark or cambial tissue is preferred.

To prevent contamination of the culture, the tissue should be surface-sterilized prior to introducing it to the culture medium. Any conventional sterilization technique, such as chlorinated bleach treatment would be effective. In addition, antimicrobial agents such as cefoxitin, benlate, cloxacillin, ampicillin, and phosphomycin at the rate of 50–500 $\mu$g/ml may provide an added margin of security.

Under appropriate conditions plant tissue cells may undergo dedifferentiation, i.e., change to precursor cells and form a tissue known as callus. Also, cambial cells may divide to form callus which may partially differentiate. Dedifferentiated cells or callus may be grown either as solid tissue or, preferably, as a cell suspension of single cells or small groups of cells in a culture medium. Metabolic products of the callus, such as taxol or other alkaloids, may be isolated from the callus cells or from the culture medium.

A suitable culture medium for callus induction and subsequent growth is an aqueous or agar solidified medium of Gamborg's B5 (Table I) supplemented with ingredients described in Table II. It is understood that modifications may be made in this medium such as substitution of other conventional salt compositions (e.g., Lloyd and McCown's or Anderson's), addition or deletion of various components, or alteration of proportions. For example, we have found that additional ammonium nitrate increased the growth rate. Thus, it is apparent that determination of suitable and optimum media for induction and growth of callus would be within the ability of a person skilled in the art.

The medium may be gelled with agar or other gelling agent such as carrageenan, preferably in an amount of 0.8–1.0%; other amounts, such as within the range of 0.1–5%, could also be used depending upon the desired consistency. However, the agar tends to interfere with the isolation of the alkaloids from the medium subsequent to culturing. We therefore prefer a liquid culture which would constitute a suspension of cells or other condition which allows removal of the culture supernatant for extraction purposes.

Temperatures in the range of about 20°–25° C. are preferable for inducing and growing the cell cultures, but temperatures greater or lower could also be used. Darkness is preferred for growth of the cell cultures. Generally, callus induction from plant tissue requires 2 weeks to 4 months. Under the above-described conditions, callus cultures on agar plates are subcultured at 2–6 month intervals, during which time they maintain a steady growth and may include a lag time before growth occurs. The cells that are grown in suspension culture are subcultured at 3–4 week intervals, during which cell mass increases 5–10 times. Cells grown in a bioreactor will have a growth rate dependent on the vessel characteristics.

Taxol is produced during cell culture and is present in the culture supernatant, especially during the 2–4 weeks following subculture. Taxol production can also be induced by the addition of various compounds, which include fungal elicitors and vanadyl sulfate, but it may well be induced by other compounds, e.g., 3,4-dichlorophenoxy triethyl(amine), etc., which also stimulate production of secondary products. The capacity for rapid induction by the fungal elicitors and other compounds will greatly benefit the commercial production of taxol. Various fungal species elicit taxol production; examples of fungal elicitors include *Cytospora abietis*, ATCC No. 38688, and *Penicillium minioluteum* (Dierckx), NRRL 18467.

TABLE I

| Compound | mg/l | mM | Compound | Amount/l |
|---|---|---|---|---|
| $NaH_2PO_4.H_2O$ | 150 | 1.1 | $MnSO_4.H_2O$ | 10 mg |
| $KNO_3$ | 2500 | 25.0 | $H_3BO_3$ | 3 mg |
| $(NH_4)_2SO_4$ | 134 | 1.0 | $ZnSO_4.7H_2O$ | 2 mg |
| $MgSO_4.7H_2O$ | 250 | 1.0 | $Na_2MoO_4.2H_2O$ | 250 μg |
| $CaCl_2.2H_2O$ | 150 | 1.0 | $CuSO_4$ | 25 μg |
| $FeSO_4.7H_2O$ | 28 | | $CoCl_2.6H_2O$ | 25 μg |
| Nicotinic acid | 1 | | KI | 750 μg |
| Thiamine.HCl | 10 | | Sucrose | 20 g |
| Pyridoxine.HCl | 1 | | | |
| m-Inositol | 100 | | pH 5.5 | |

TABLE II

| Compound | Amount per liter |
|---|---|
| Casamino acids | 2 g |
| 2,4-Dichlorophenoxyacetic acid | 20 ml of a 100 mg/l stock |

Taxol was produced also when cells were encapsulated in calcium alginate beads, as well as when in a slurry made by incorporation of 0.1% agar into the media. This gives added flexibility in the choice of scale-up production methods.

The compounds produced by the cell cultures are taxol and a number of additional compounds, some of which may not be present in the plant. The structural formula of taxol and related compounds are given in Wani et al. [J. Am. Chem. Soc. 93: 2325–2327 (1971)] and in a series of articles by Kingston [e.g., Lloydia 45: 466–470 (1982)].

Recovery of taxol from the culture supernatant is easily accomplished. However, adsorbent beads further expedite recovery of taxol. Beads remaining in the culture during the production of taxol may also allow greater production by binding the taxol. Recovery of taxol from the cell cultures or beads may be by any conventional procedure as known in the art. For example, the extraction of taxol from the cell supernatant or beads is readily accomplished with ether or methylene chloride. Extraction of taxol from the supernatant or beads instead of from tissue will be commercially expedient.

As stated above, many plants are known to produce alkaloids in tissue culture, but quite often the compounds produced are not typical of the parent plant. While not desiring to be bound to any particular theory of operation, the surprising production of taxol in cell culture may be due to the conditions to which the cells are subjected.

The following examples are intended only to further illustrate the invention and are not intended to limit the scope of the invention which is defined by the claims.

EXAMPLE 1

Plant material of *T. brevifolia* was collected from a forest and stored at 4° C. until processed. The plant material consisted of slabs of tree bark (cut at a depth reaching into the wood), stems, and needles. The ages of trees were represented by old (12-inch diameter), middle (3-inch), and young (1.5-inch) because more taxol is produced in the older trees. The bark samples were given the most attention because this is where the highest concentration of taxol is found. Bark samples were surface sterilized the longest by immersing in chlorinated bleach (clorox) for 30–45 seconds, followed by five water rinses. All procedures utilized sterile techniques. The samples were then cut with a scalpel into 0.5–1.0 cm squares and transferred by forceps to agar media. The squares of tissue were sometimes cut again into cambium, or cambium and inner phloem, and outer phloem regions of the bark. In some cases the wood region was retained on the sample. Medium used was Gamborg's B5 (Tables I and II); it was dispensed into 15×60 mm petri dishes. Antimicrobial agents were added to the medium to limit growth of contaminating microorganisms; these agents were: an antibiotic, Cefoxitin (obtained from Merck, Sharp, & Dohme Co.), at 0.1 ml/100 ml medium, using a 25 mg/ml stock; and a fungicide, Benlate (obtained from the duPont Co.), at 0.5 ml/100 ml medium, using a 0.5% stock. Callus proliferation occurred 2 weeks to 4 months later. The callus has been successfully subcultured repeatedly, and some subcultures eventually gained a greater growth rate.

EXAMPLE 2

Example 1 was repeated, except that plant tissue was used to initiate the callus on additional variations of the Gamborg's B5 medium and was collected from other locations at another time of year. The variations included those mentioned in Example 4 in regard to the amount of ammonium nitrate and the basal salts source. In addition, some were supplied with napthalene acetic acid (NAA), added at 5 ml/l of a 100 mg/l stock instead of 2,4-D. Again, callus proliferation occurred. The best proliferation occurred on the media used in Example 1.

EXAMPLE 3

Callus from Example 1 was introduced into suspension cell culture. Subcultures were made into 15 ml of Gamborg's B5 medium in 125 ml Erlenmeyer flasks containing various amounts of the hormones 2,4-D, Kinetin, NAA, or 6-benzylaminopurine (BAP) and shaken at 110–125 rpm. Relative growth was: 5–10 ml of 2,4-D stock/l >20 ml of 2,4-D>5–10 ml of NAA stock/l. Kinetin or BAP did not increase the growth occurring with 2,4-D or NAA.

EXAMPLE 4

Subcultures from suspension cells of Example 3 were divided into: (1) Gamborg's B5 medium (Tables I and II) with or without a supplement of ammonium nitrate; (2) Lloyd and McCown's woody plant basal salts mixture (Table III), 5 ml Murashige and Skoog's modified vitamin mixture (Table IV), 15 g sucrose, 2 g casamino acids, and 5 ml 2,4-D; or (3) Anderson's rhododendron basal salt mixture (Table III), 5 ml Murashige and Skoog's modified vitamin mixture, 15 g sucrose, 2 g casamino acids, and 5 ml 2,4-D. Inoculum consisted of 20 μl of cells placed in 45 ml of media in a 125-ml Erlenmeyer flask. Growth of cells in media 2 and 3, as well as the ammonium-supplemented Gamborg's B5, was 2-3 times greater than in unsupplemented Gamborg's B5. Duplicate flasks at 27° C. and 20°-25° C. showed greater growth at 20°-25° C. than at 27° C. and greater growth in darkness than in light. Taxol was produced by cells grown in media 1 and 2 during the 2-4 week period following subculture.

EXAMPLE 5

Taxol or taxol-like activity was demonstrated by utilizing an in vitro microtubule polymerization assay. Microtubules were isolated from calf brain or from rat brain [Margolis et al., Biochemistry 20: 4451-4458 (1981)]. Assembly of microtubules in the absence of guanosine triphosphate (GTP) was promoted by the taxol standard from the National Cancer Institute at 1-10 μM concentrations and by concentrated or ether extracts of the suspension cell cultures. Concentrated tissue culture media alone or microtubules alone were used as negative controls in these experiments.

TABLE III

| Component | McCown[a] mg/l | Anderson[b] mg/l |
| --- | --- | --- |
| $NH_4NO_3$ | 400.0 | 400.0 |
| $H_3BO_3$ | 6.2 | 6.2 |
| $CaCl_2$ | 72.5 | 332.0 |
| $Ca(NO_3)_2.4H_2O$ | 556.0 | |
| $CoCl_2.6H_2O$ | | 0.025 |
| $CuSO_4.5H_2O$ | 0.25 | 0.025 |
| $Na_2.EDTA$ | 37.3 | 74.5 |
| $FeSO_4.7H_2O$ | 27.8 | 55.7 |
| $MgSO_4$ | 180.7 | 180.7 |
| $MnSO_4$ | 22.3 | 16.9 |
| $NA_2MoO_4.2H_2O$ | 0.25 | 0.25 |
| KI | | 0.3 |
| $KNO_3$ | | 480.0 |
| $NaH_2PO_4.H_2O$ | | 380.0 |
| $KH_2PO_4$ | 170.0 | |
| $K_2SO_4$ | 990.0 | |
| $ZnSO_4.7H_2O$ | 8.6 | 8.6 |

[a] W. C. Anderson, Proc. Int. Plant Prop. Soc. 25: 129-134 (1975)
[b] G. Lloyd and B. McCown, Proc. Int. Plant Prop. Soc. 30: 421-427 (1980)

TABLE IV

| Component | mg/l |
| --- | --- |
| Glycine | 2.0 |
| myo-Inositol | 100.0 |
| Nicotinic acid | 0.5 |
| Pyrodoxine HCl | 0.5 |
| Thiamine HCl | 1.0 |

EXAMPLE 6

Taxol production by cell suspension cultures was determined by analysis with high performance liquid chromatography. The suspension was divided into cell and supernatant fraction, frozen at −20° C., and extracted with ether.

The identification of taxol from Taxus tissue cultures was accomplished by HPLC on a Hewlett-Packard 1090 equipped with a diode array detector and a C-18 reversed phase column (3.9 mm×30 cm; Waters μBondapak) heated to 34° C. An isocratic flow of 0.1% TFA (aq)/acetonitrile (53/47) was used to optimize the separation of taxol from other compounds found in the culture filtrate. The retention time of a standard sample of taxol obtained from the National Cancer Institute is 14.3 minutes. Detection at 227 nm was found to be the optimal wavelength.

Using the above conditions, the peak identified as taxol has a retention time of 14.3 min. From the integration of the peak in the spectrum there is calculated to be 0.8 ng/mAU (AU=Absorbance Units) for taxol. The concentration of taxol in the supernatant was in the range 1.0-3.0 mg/l.

EXAMPLE 7

Taxus needles were used to initiate callus by the procedures of Examples 1 and 2. The callus was placed into suspension mixture. Analysis of the culture supernatant by HPLC was positive for taxol.

EXAMPLE 8

Subcultures from suspension cells of Example 3 were grown as in Example 4. Fungal cultures were grown in Gamborgs B5 and used to induce taxol production. Autoclaved mycelia and filter-sterilized culture filtrates caused induction of taxol production as measured by HPLC analysis of the plant cell supernatant. *Cytospora abietis*, ATCC #38688, was among the fungi which induced taxol. Taxol could be induced as early as 26 hr after addition of the fungal material.

EXAMPLE 9

Subcultures from suspension cells of Example 3 were grown as in Example 4, except the cells were encapsulated in calcium alginate beads. The beads were made by mixing cells with Bellco Glass Co. liquid sodium alginate and dropping the mixture through an 18-gauge needle into the plant cell media containing 50 mM calcium chloride. Beads were rinsed before culturing. Encapsulated suspension cells also produced taxol as measured by HPLC.

EXAMPLE 10

Subcultures from suspension cells of Example 3 were grown as in Example 4, except that 0.1% Difco Bacto agar was added to the media to produce a slurry. Slurried suspension cells also produced taxol as measured by HPLC.

EXAMPLE 11

Subcultures from suspension cells of Example 3 were grown as in Examples 4, 8, 9, and 10. Nonionic polymeric adsorbent beads Amberlite XAD-2 were added to the cultures either loosely or in dialysis tubing. All the taxol in the culture supernatant became bound to the beads. The beads were added to the cultures at sampling intervals or remained in the culture to continuously remove the product. The dialysis bags were readily removed and placed in the extraction solvent. The taxol was recovered by diffusion through the dialysis membrane or by opened ends of the membrane. The molecular weight cut-off of the membrane further assisted purification of taxol from the other components in the supernatant. Similarly, Sep-pak $C_{18}$ cartridge (Waters Associates) bound taxol and was also used for recovery of taxol.

EXAMPLE 12

Best mode of taxol production: Stocks are maintained on agar plates and periodically serve to initiate new suspension cultures. Subcultures from suspension cells derived from bark or cambial cells in Example 1 were grown as in Example 3. Inoculum was a 20 μl volume of cells per 45 ml of Gamborgs B5 in 125 ml Erlenmeyer flasks containing 5 ml of 2,4-D stock/liter. Cells were grown shaking at 110-125 rpm in the dark at 20°-25° C. Rapid production of taxol was achieved by addition of autoclaved *Cytospora abietis* mycelia homogenate at 2 ml per flask, as was done in Example 8. Adsorbant beads of 2 ml volume are added to the media as in Example 11 to adsorb taxol. The beads are collected and extracted with 10 ml methylene chloride to obtain taxol. Methylene chloride is evaporated with nitrogen gas and heat, and then 600 μl acetonitrile is added. The sample is analyzed by HPLC as in Example 6 by comparing the elution profile to a standard taxol sample.

It is understood that the foregoing detailed description is given merely by way of illustration and that modification and variations may be made therein without departing from the spirit and scope of the invention.

We claim:

1. A method of producing taxane ring-containing alkaloid compounds from cell cultures of *Taxus brevifolia* comprising the steps of:
   a. providing living tissue of said *Taxus brevifolia*;
   b. providing a nutrient culture medium suitable for said cell culture formation from said tissue;
   c. culturing said tissue on said medium to produce calli or cell suspensions derived therefrom and
   d. recovering said taxane ring-containing alkaloid compounds from said calli or suspension culture.

2. The method as described in claim 1 wherein said living tissue in step (a) is selected from the group consisting of bark, cambial tissue, needles, and roots.

3. The method as described in claim 1 wherein said recovery is from said calli.

4. The method as described in claim 1 wherein said recovery is from said cell suspension.

5. The method as described in claim 1 wherein said cell culture comprises cells held in a matrix formed by a gelling agent.

6. The method as described in claim 5 wherein said matrix is formed from agar.

7. The method as described in claim 1 wherein said cell culture is encapsulated into capsules.

8. The method as described in claim 7 wherein said capsules are formed from calcium alginate.

9. The method as described in claim 1 wherein said alkaloid compound is taxol.

10. The method as described in claim 1 wherein an inducer is added to step (c) in an amount sufficient to increase alkaloid production.

11. The method as described in claim 10 wherein said inducer is autoclaved mycelia or sterilized culture filtrates of *Cytospora abietis*, ATCC No. 38688.

12. The method as described in claim 10 wherein said inducer is autoclaved mycelia or sterilized culture filtrates of *Penicillium minioluteum* (Dierckx), NRRL 18467.

13. The method as described in claim 10 wherein said inducer is vanadyl sulfate.

14. The method as described in claim 1 wherein said medium is Gamborg's B5, with 2,4-dichlorophenoxy acetic acid or naphthalene acetic acid added as a growth hormone.

15. The method as described in claim 1 wherein said medium is Lloyd and McCowns medium.

16. The method as described in claim 1 wherein said culture medium contains an antimicrobial agent selected from the group consisting of cefoxitin, benlate, and cloxacillin.

17. The method as described in claim 1 wherein said recovery is accomplished by adsorbing said alkaloid compounds onto polymeric adsorbent beads, separating said beads from said culture medium, and extracting said alkaloid compounds from said beads.

18. The method as described in claim 1 wherein said culture medium contains ammonium nitrate.

* * * * *